United States Patent [19]
Hoffman

[11] Patent Number: 4,649,923
[45] Date of Patent: Mar. 17, 1987

[54] TEMPERATURE INDICATING ELECTROTHERAPY ELECTRODE

[75] Inventor: Kent C. Hoffman, Cockeysville, Md.

[73] Assignee: Murray Electronics Associates Limited, Hunt Valley, Md.

[21] Appl. No.: 788,216

[22] Filed: Oct. 16, 1985

[51] Int. Cl.⁴ ............................................. A61B 5/04
[52] U.S. Cl. ................................... 128/641; 128/736; 128/798
[58] Field of Search ............... 128/639, 640, 641, 798, 128/802, 803, 736; 374/162

[56] References Cited

U.S. PATENT DOCUMENTS

| | | | |
|---|---|---|---|
| 3,704,625 | 12/1972 | Seto et al. | 374/162 |
| 3,720,209 | 3/1973 | Bolduc | 128/416 |
| 3,746,004 | 7/1973 | Jankelson | 128/803 |
| 3,951,133 | 4/1976 | Reese | 73/356 |
| 3,972,329 | 8/1976 | Kaufman | 128/641 |
| 4,016,761 | 4/1977 | Rozzell et al. | 73/356 |
| 4,080,959 | 3/1978 | Leveen | 128/736 |
| 4,213,463 | 7/1980 | Osenkarski | 128/639 |
| 4,300,575 | 11/1981 | Wilson | 128/802 |
| 4,302,971 | 12/1981 | Luk | 128/736 |
| 4,331,161 | 5/1982 | Patel | 128/736 |
| 4,378,808 | 4/1983 | Lichtenstein | 128/736 |
| 4,524,087 | 6/1985 | Engel | 128/639 |

Primary Examiner—William E. Kamm
Assistant Examiner—Randy Citrin
Attorney, Agent, or Firm—Nixon & Vanderhye

[57] ABSTRACT

Apparatus for applying an electric or electromagnetic signal to the skin and tissue of a living body surface, and for measuring the physiological responses of the skin and tissue to the electric or electromagnetic signal is disclosed. The apparatus comprises a conductive patch electrode applicator, a temperature responsive liquid crystal layer applied to said conductive patch, and an adhesive boundary extending at least part way about the edges of the electrode applicator or coil applicator.

12 Claims, 8 Drawing Figures

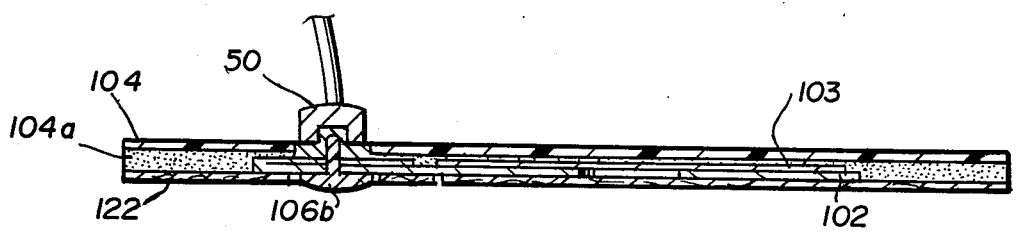
IFIG. 3
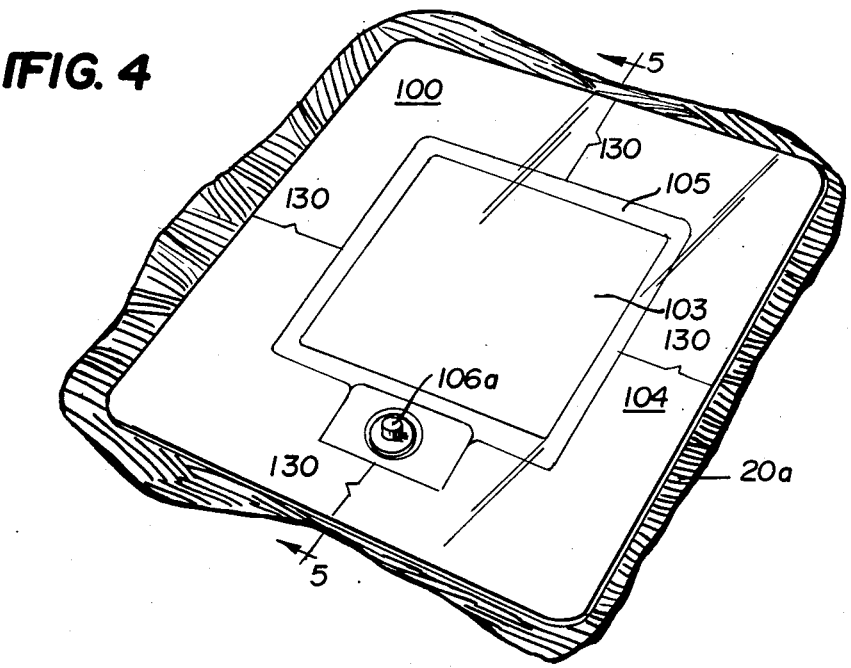
IFIG. 4
IFIG. 5
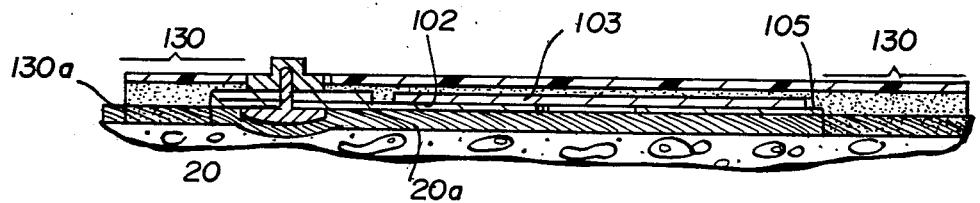

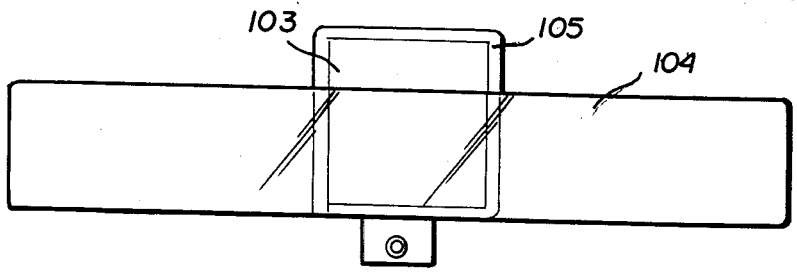
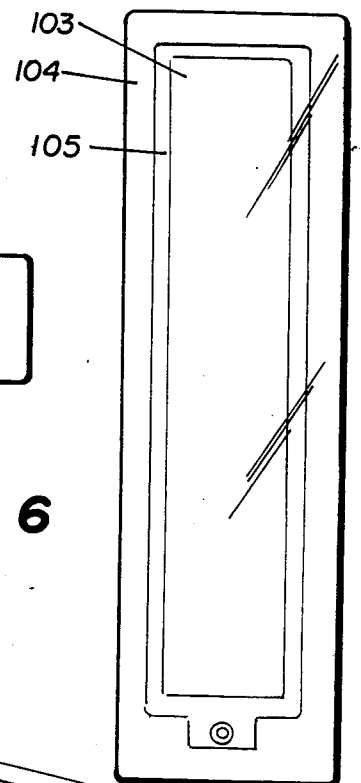
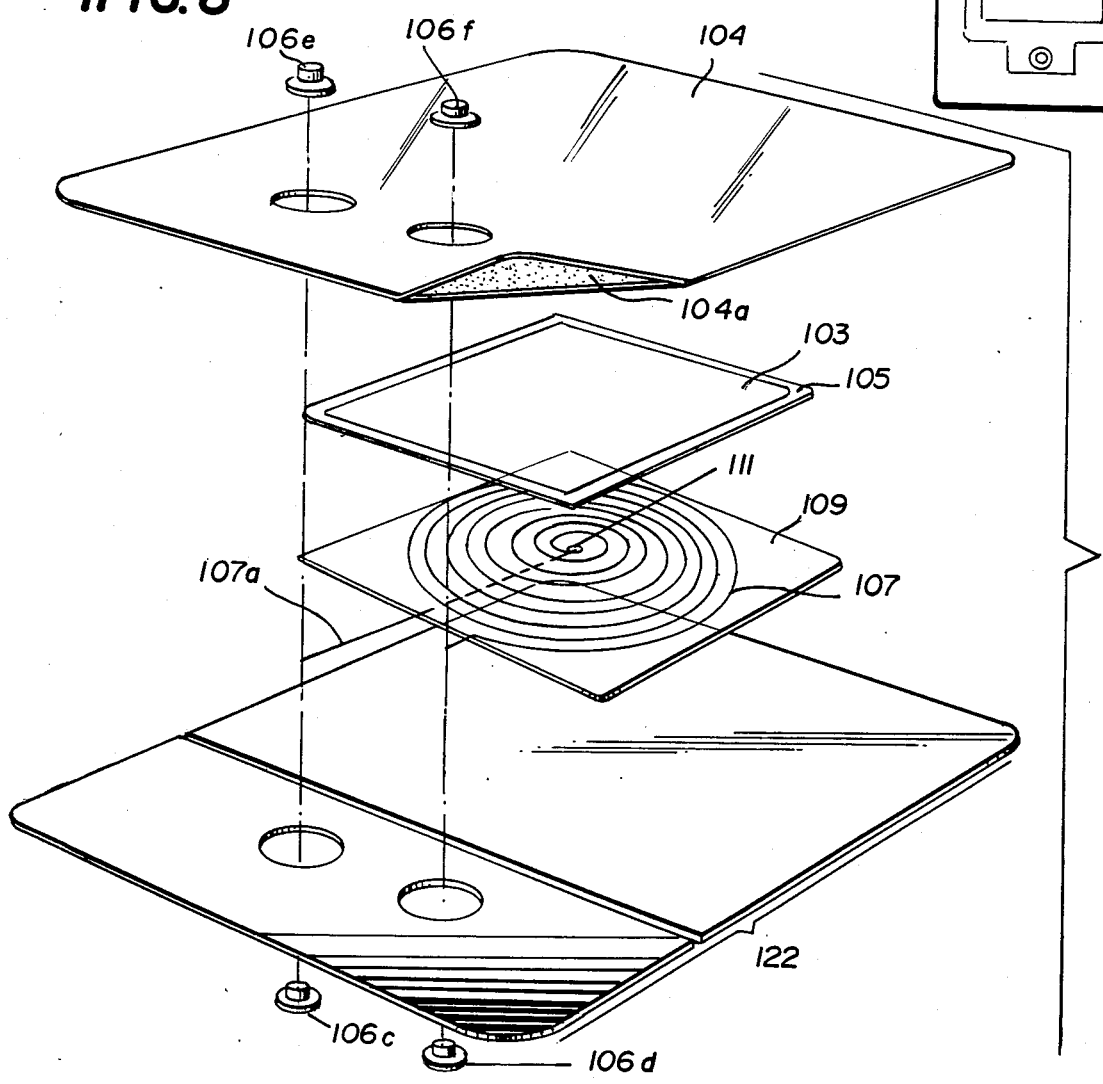

TEMPERATURE INDICATING ELECTROTHERAPY ELECTRODE

This invention is generally directed to a temperature indicating electrotherapy electrode/coil for therapeutic and diagnostic applications in medical and veterinary use. The subject invention is related to the copending and commonly assigned applications Ser. Nos. 711,044 and 788,215 filed Oct. 16, 1985 and 783,093 filed Oct. 2, 1985, the entire disclosures of which are hereby incorporated by reference.

BACKGROUND OF THE INVENTION

It is often necessary to establish a localized electrical contact with the external body surface of a living subject. Such contact is typically achieved by the use of electrically conductive electrodes having extended surface areas placed in electrical contact with a desired portion of an external body surface through an intermediate electrode gel, liquid or other preparation designed to ensure good and continuous electrical contact between the living body surface and the conductive electrode surface. Such electrical connections to living subjects are now commonly required for therapeutic and diagnostic applications in both medical and veterinary usage. For example, electro-therapeutic stimulation has now been recognized to promote the healing of bones and other body tissues and/or to have other advantageous physiological effects. Many diagnostic techniques (e.g., electrocardiograms) also require electrical connections to body surfaces so as to monitor electrical body surface potentials.

Medical research has applied advanced temperature measurement techniques such as infrared thermography and liquid crystal films to diagnose and identify various forms of vascular diseases and tumors. Since temperature is an indicator of circulatory function, techniques have been developed to measure the effects of nerve blocking drugs on the circulatory system by measuring temperature. In addition to diagnostic applications, temperature measuring devices have been used in medicine to locate everything from veins to placental attachment sites. A recent invention using liquid cyrstals, U.S. Pat. No. 4,378,808, can be used to detect unwanted infusion of fluids into tissue when an IV fails.

U.S. Pat. No. 4,213,463 discloses a body electrode with a physically movable visual indicator comprising a flap imprinted with areas of green and red, supposedly designed to ensure optimal parallel positioning and electrical current distribution. U.S. Pat. No. 4,016,761, discloses a probe using liquid crystals and optical fibers for measuring temperature changes of tissue while the tissue is being irradiated with microwaves. U.S. Pat. No. 3,951,133 employs tin foil as a liquid crystal substrate but there is no suggestion that the tin foil might be utilized as an electrode.

Temperature measurement has also been applied for therapeutic use in the field of bio-feedback. A variable signal tone, light or meter provides the patient with a feedback signal that relates to the patient's skin temperature. The patient is trained to respond to this type of feedback by modifying his temperature and behavior.

Electrotherapy devices have heretofor employed meters, lights, or tone generators to indicate the voltage/current that is applied to a patient's electrodes (or to the treatment coils in the case of pulsed magnetic field devices). Lights and meters have also been used to indicate the current that passes through a patient. These conventional techniques measure some form of electricity in order to show that a signal is applied to or present in the patient. They do not, however, indicate the quality of the physiological link between the electrotherapy device and the patient. There is a critical need for an electrotherapy device to conveniently and accurately monitor the quality of the electrical connection and the quality of the resulting physiological effects during the electrotherapy process.

In addition to temperature changes that occur due to disease and the body's response to drugs, temperature changes that result from various forms of electrotherapy have been studied. Several studies have shown that skin temperature will rise in response to electrical signals produced by certain transcutaneous electrical nerve stimulators (TENS) that are applied to control pain. Other types of electrotherapy devices cause skin temperature to drop while achieving inflammation reduction and tissue repair. Improved local circulation by increased vascularization, or alternating vaso-dilation and vaso-constriction will be indicated by a rise in temperature.

SUMMARY OF THE INVENTION

This invention utilizes temperature sensing liquid crystals coated on an electrode applicator or coil applicator surface as a direct temperature indicator to show how well an electrotherapy system is functioning and whether the applied electrical or magnetic field dose is producing the expected temperature response in the patient's body tissue and/or the presence of other physiological effects.

Additional advantages are available from use of the invention. For example, electrodes are normally held in place with a variety of bandages, wraps, tapes, adhesive films and adhesive gels that often fail to maintain proper electrical contact between the electrode and the surface of the patient. This new temperature sensing electrode applicator readily and directly indicates intermittent or irregular electrical contact as it occurs so that it can be corrected.

Correct current density at the electrode site also may be an important factor making it even more vital to monitor uniform electrode contact with the tissue. Constant current electrotherapy stimulators, for example, can cause tissue necrosis and burns at the electrode site when incomplete electrode contact causes current density to rise. For other types of electrotherapy devices the "biological window" may be missed when proper current density is not maintained under the electrode.

This invention effectively monitors the mechanical/electrical contact between electrode and skin to prevent injury while, simultaneously monitoring the physiological response of the body to the applied electrotherapy signal.

Similar benefits are available when employing this invention with an electromagnetic coil applicator rather than an electrode applicator. The placement of the treatment coils is critical to the nature of the electromagnetic field that is to be induced into the tissue. This invention directly indicates, by measuring temperature, physical movement of the coil applicator away from the surface of the patient, and thus alerts the user to a condition that reduces or eliminates the effectiveness of the electrotherapy treatment. It also measures the physiological response of the patient via detected local skin temperature changes.

In brief summary, the exemplary embodiment of this invention provides a conductive patch electrode applicator or coil applicator, a liquid crystal layer applied to said conductive patch electrode applicator or coil applicator, and an adhesive boundary extending at least part way about the edges of the electrode applicator or coil applicator.

The adhesive boundary may comprise a relatively larger adhesive-backed, flexible insulating sheet patch having a relatively smaller conductive patch with its associated liquid crystal layer being affixed therewithin (on the adhesive-coated side). The adhesive-coated border around at least a portion of the conductive patch electrode applicator, or coil applicator (and preferably completely thereabout) permits the applicator to be adhesively affixed to treatment locations where electrodes cannot easily be affixed by traditional wrapping techniques. Such an adhesive border forms an occlusive seal with hair (or fur) and external body tissue surfaces at a time when the treatment site is still relatively clean and dry.

To facilitate storage, transport, etc., a releasable liner is also preferably included and is releasably attached to and covering the otherwise exposed adhesive-backing of the insulating sheet prior to its intended usage. Such a release liner typically is formed of two parts so that the flexible electrode assembly can be slightly flexed to permit easy fingertip access to an edge of the liner thus facilitating its easy removal just prior to the time of intended usage.

An electrical snap-on connection terminal(s) is preferably affixed to the conductive patch electrode applicator and extends backwards through a further aperture in the insulating sheet so as to permit ready electrical connection of a suitable electrical lead from an electrical signal generator or other conventional treatment-/diagnostic apparatus.

The conductive patch electrode applicator portion of the assembly is preferably flexible and may be formed from a thin metal foil patch pre-laminated to its own thin insulating coating so as to provide added structural strength.

These as well as other objects and advantages of the invention will be better appreciated by carefully reading the following detailed description of the presently preferred exemplary embodiments of this invention taken in conjunction with the accompanying drawings.

BRIEF DESCRIPTION OF THE DRAWINGS:

FIG. 3 is a cross-sectional view of the assembled temperature electrode applicator of FIG. 2;

FIGS. 4-5 are perspective and cross-sectional views of the FIG. 2 embodiment in place with the external body surface of a living subject.

FIGS. 6 and 7 are plan views of two further exemplary embodiments of the electrode applicator structure.

FIG. 8 is an exploded perspective view similar to FIG. 2 but having an inductive coil applicator in place of a solid electrode applicator.

DETAILED DESCRIPTION

The temperature indicating electrotherapy electrode applicator or coil applicator of this invention utilizes liquid crystals associated therewith. The liquid crystals indicate, for example, whether the electric/magnetic field dose is producing the expected physiological temperature response. The temperature indicating electrotherapy electrode applicator, or coil applicator also indicates the quality of contact between an applicator and the surface of the area being treated.

The exemplary temperature electrode applicator uses a conductive film layer (with an associated electrical connector), having a liquid crystal film layer thereon (preferably with a color-temperature reference coating as a border) and carried by a clear plastic film layer with adhesive backing (preferably including a release liner). The conductive film layer is applied to the skin and serves both as an electrode applicator to deliver the electrical signal to the skin and as a substrate for the liquid crystal layer (and its color-temperature reference layer).

Figure 1:
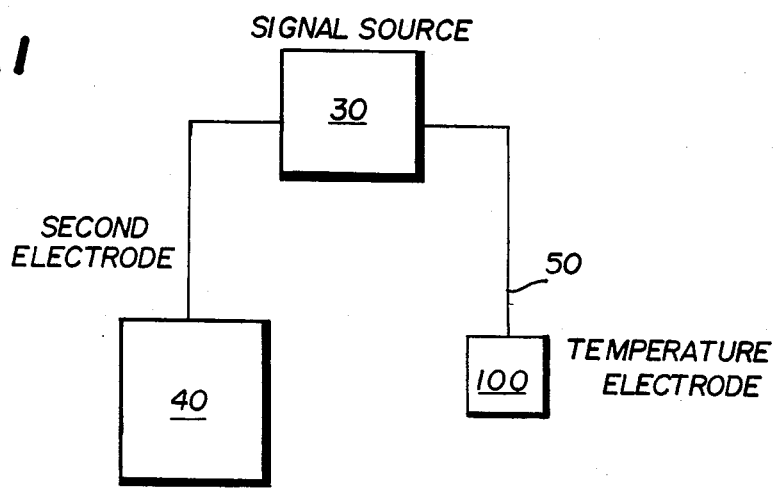
FIG. 1 is a general perspective view of the invention in combination with a large electrode and a signal source.

Typically, as shown in FIG. 1 an electrode 40, of relatively large area is utilized as an anode while a relatively smaller electrode 100 is applied near a desired treatment site (so as to provide an increased physiologically significant electrical current density thereabout) as a cathode electrode and connected to the signal source 30 by lead wire 50. Electrical signals are then conventionally applied to the electrodes so as to achieve desired treatment effects.

In some applications, larger electrode 40 is utilized as a cathode while the smaller electrode 100 is the anode. Furthermore, some signal sources e.g. transcutaneous, electrical nerve stimulators (TENS), supply biphasic signals to the electrodes, i.e. alternating current or waveforms with both positive and negative components. The present invention can be used with a biphasic signal having the smaller electrode 100 relatively close to the treatment site and the larger electrode 40 at a more remote location. This arrangement insures a higher density at the treatment site and a lower, non-biologically stimulating, signal at the larger electrode 40.

Figure 2:
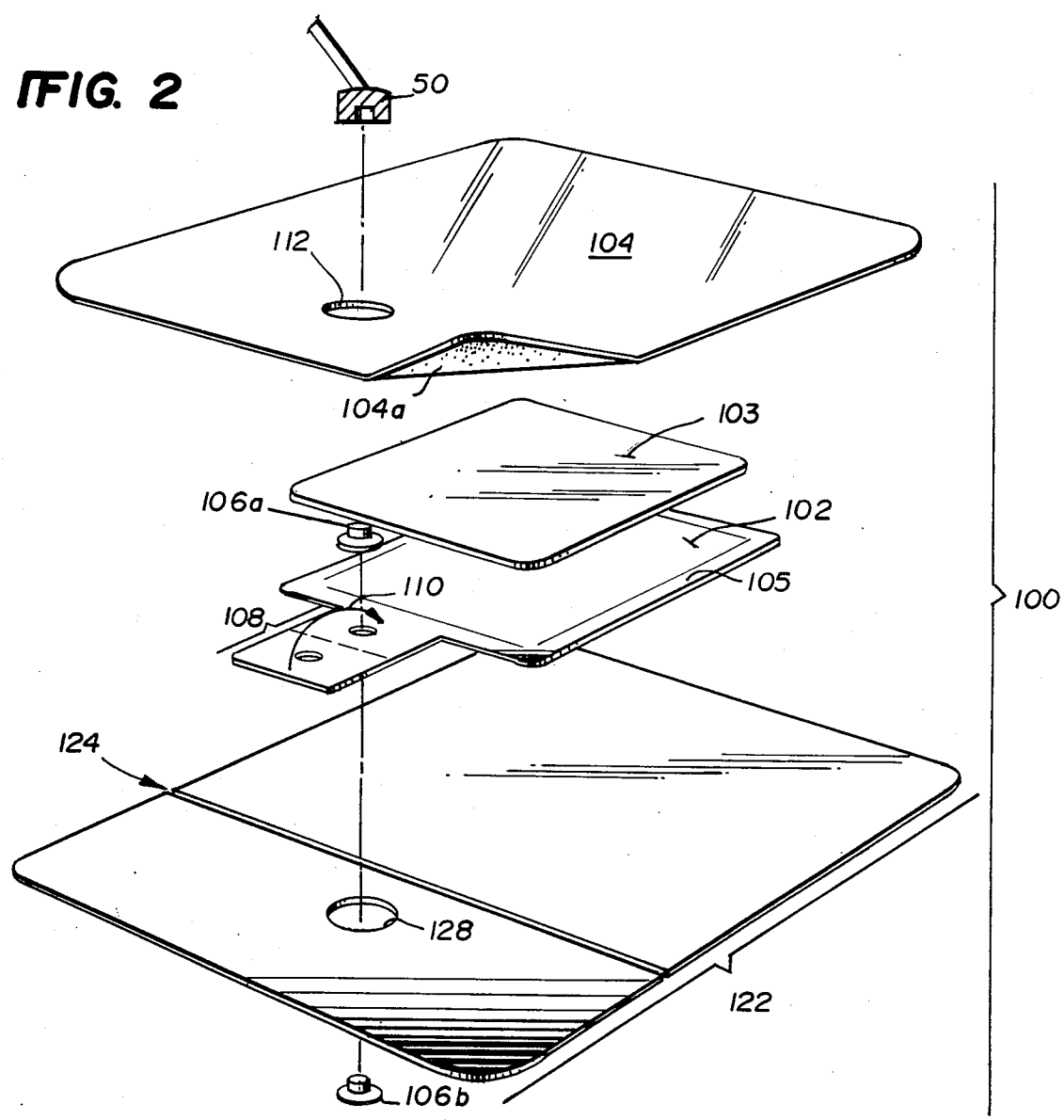
FIG. 2 is an exploded perspective view of the various components used in an exemplary embodiment of the adhesively applied temperature electrode applicator of this invention.

Electrode 100 is shown in more detail at FIGS. 2 and 3. A conductive metal foil 102 constitutes the active electrode surface. In the exemplary embodiment, foil 102 is actually a very thin (e.g., 0.00035 inch) layer of aluminum foil pre-laminated to a very thin (e.g., 0.00092 inch) layer of polyester film (laminated to the top of structure 102 as seen in FIG. 2) so as to provide added structural strength.

The top film layer 104 with its adhesive backing 104a on its lower surface is larger than the underlying layers so that a band of adhesive is exposed around the outside of the lower layers. This adhesive band holds the lower layers in place on the skin by adhering to the skin or body surface. The top film layer 104 with its adhesive backing 104a is clear to permit viewing of the liquid crystal layer 103 and color-temperature reference border 105 while adhering to and providing protection to the lower layers.

The laminated aluminum foil/polyester film 102 may be cut from commerically available material (e.g. part No. 1035 from Lam-A-Shield Incorporated, Cleveland, Ohio). The presently preferred adhesive-backed patch 104 also cut from commerically available material (e.g. part No. 7350 from 3M Corporation which comprises a thin (e.g., 0.002 inch) insulating sheet of polypropylene with a thin (e.g., 0.0008 inch) coating of acrylic adhesive 104 on one side.

The liquid crystal film layer 103 is preferably sensitive to physiological temperature changes in the range of 26° C. to 36° C., which includes the normal skin temperature range of 30° C. to 33° C. The liquid crystal layer 103 thus changes color with the changing skin temperature during application of the electrical signal or magnetic field to the skin via the conductive film layer.

The border 105 is printed on foil 102 (as shown in FIG. 2). In an alternative embodiment, the border 105 is part of the liquid crystal film layer 103. The border 105 is printed with a fixed color scale and related temperature values that correspond to the possible different liquid crystal colors.

A set of snaps or other connectors is attached to the conductive film layer to provide electrical contact with the wires and the electric signal source, or the electrical signal source that drives the coil. The conventional snap-on type electrical connector comprising mated parts 106a and 106b is attached to a folded-over tab portion 108 of the laminated aluminum foil structure 102. Since it is folded over (as indicated by arrow 110), a conductive aluminum foil surface is exposed on both the top and bottom of the thus double thickness tab portion 108 for increased structural support and electrical area connection with the snap-on devices 106a, 106b. The snap-on connector part 106a has a connector projection which extends backwardly (i.e. upwardly in FIG. 2) through an aperture 112 in the insulating patch 104 so as to be readily available for snap-on electrical connection to lead wire 50 (as shown in FIG. 2).

The flexible electrode assembly of FIGS. 2-3 also includes a releasable liner layer 122 which is normally in place covering the otherwise exposed portions of the adhesive surface 104a until the intended time of usage. Typically, the release liner 122 will include a break 124 so that the entire assembly may be slightly bent at the break to gain finger access to a free edge of the releasable liner 122 and thus facilitate its strippage from the adhesive layer 104a and ready the assembly for adhesive affixation to the desired body surface area.

Release liner 122 is shown as including aperture 128. Aperture 128 typically occurs because it permits the assembly of snap-on connector 106a, 106b while the release liner 122 remains in place thus protecting the adhesive layer 104a during manufacturing processes. However, it will be appreciated that such apertures are not required since the release liner 122 is typically removed before the remainder of the electrode assembly shown in FIGS. 2-3 is adhesively affixed to a desired body surface site and used.

FIG. 4 depicts the electrode 100 of FIGS. 2-3 with the releasable liner 122 removed and the remainder of the assembly adhesively secured in place to a desired external body surface 20a of a living subject. Typically, the treatment site 20a should be clean and the connector end of cable 50 may be snapped onto the snap connector 106a prior to installation of the electrode patch 100 onto the treatment site. Once the protective releasable liner 122 has been removed so as to expose a boundary 130 of adhesive 104a (extending all about the centrally located conductive patch 102 in the exemplary embodiment), the assembly may be positioned as desired over site 20a and pressed firmly thereto so as to assure a good adhesive bond. As shown in the cross-sectional view of FIG. 5, the boundary areas 130 will include an adhesively sealed and occluded area 130a which incorporates any contiguous body hair (or fur) so as to provide a substantially impervious seal between the external surface of living body 20 and the periphery of the conductive electrode 102.

When the electrode structure is to be used on horses, it has been experimentally determined that the border area 130 of adhesive available for affixation should probably be at least about 0.75 inches wide to insure good adhesive affixation. Preferably, such adhesive is provided in a substantially continuous border 130 all about the conductive patch 102. However, as should be appreciated, for some applications it may not be necessary to have such a continuous enclosure of the electrode/gel/skin interface. FIG. 7, for example, depicts an alternate embodiment without such a continuous adhesive border.

As should be appreciated, other electrode shapes may utilize the principles of this invention and, for example, an elongated rectangular electrode is depicted in FIG. 6. Similarly, as earlier mentioned, for some applications it may not be necessary or even desirable to have a completely continuous adhesive border about the electrode 102. Accordingly, in such cases, the adhesive-backed flexible insulating patch 104 may have a considerably different shape from that of the electrode 102 as is, for example, depicted at FIG. 7. It will also be appreciated that the adhesive backing might in some cases be applied directly to the periphery or other desired portions of the conductive electrode structure itself. The conductive patch may also be formed by printing, painting or otherwise placing conductive ink on a suitable substrate. However, in the present exemplary embodiments, aluminum foil is preferred (e.g., it is conceivable that the ions which make an ink conductive might, over time, migrate under influence of the electrical treatment fields away from the printed ink itself thus deteriorating the overall electrode function).

In the present exemplary embodiment, the electrode 102 may be approximately 3 inches square (exclusive of tab 108) while the insulating patch 104 may be approximately 5×5½ inches in overall dimension.

Another embodiment of the subject invention, the temperature indicating electrotherapy coil applicator shown in FIG. 8, utilizes a coil 107 in place of the electrode 102 of the previously described embodiments. The temperature indicating electrotherapy coil applicator is comprised of a coil 107 on the top side (side opposite the body contact side) of a flexible circuit 109. The coil 107 may be copper, or conductive ink which is printed on the flexible circuit 109. A connection terminal having parts 106d and 106f is connected to coil 107. A plated or printed through hole 111 connects the coil 107 center to a single conductive track 107a on the opposite side of flexible circuit 109. This track 107a runs towards the edge where it connects with the connection terminal having parts 106c and 106e. The track 107a need not be insulated from the skin or body. A liquid crystal film layer 103, located over the coil 107 may have a color-temperature reference coating as a border 105. The temperature indicating electrotherapy coil applicator may have a clear plastic film layer 104 with adhesive backing 104a and release liner 122.

The temperature indicating electrotherapy coil applicator is applied to the skin and serves to induce an electromagnetic field into the underlying tissues. The liquid crystal layer 103 measures the temperature changes caused by the electromagnetic field.

It will be understood that the electrode/coil apparatus and method may be utilized to achieve signal coupling with human subjects as well as animals.

Although this invention has been above-described only with respect to a few presently preferred exemplary embodiments, those skilled in the art will recognize that many variations and modifications may be made in these embodiments while yet retaining many of the novel features and advantages of this invention. The following claims are intended to cover all such variations and modifications.

What is claimed is:

1. An apparatus for applying an electric signal to the skin and tissue of a living subject, and for measuring the physiological responses of the skin and tissue to said electric signal, said apparatus comprising:
   a conductive patch having an electrical connection terminal;
   a temperature-responsive liquid crystal layer affixed to said conductive patch; and
   an adhesive boundary extending at least part way about the edges of said conductive patch.

2. An apparatus as in claim 1 wherein:
   said adhesive boundary comprises an adhesive-backed flexible insulating sheet having said conductive patch with said liquid crystal layer affixed therewithin on one adhesive-coated side; and
   further including a release liner releasably attached to and covering the otherwise remaining exposed adhesive-backing of said sheet prior to its intended usage.

3. An apparatus as in claim 2 wherein said terminal comprises an electrical snap-on terminal affixed to said conductive patch and extending through an aperture in said sheet towards the other side of said sheet.

4. An apparatus as in claim 3 wherein said conductive patch comprises a metal foil patch pre-laminated with an insulating coating on the side affixed to said liquid crystal layer and having a doubled-back tab area at which said terminal is affixed with electrical connections being effected to both the exposed top and bottom metal foil surfaces in the double thickness tab area.

5. An apparatus as in claim 1 wherein said liquid crystal layer has a border with a fixed color-temperature reference scale imprinted thereon.

6. A conductive electrode patch having an electrical connection terminal and also having a temperature-responsive liquid crystal layer permanently affixed thereon, for therapeutic or diagnostic applications in medical or veterinary use and having an attachment adhesive disposed about at least a portion thereof for adhesively attaching the electrode patch adjacent a skin surface.

7. A conductive electrode patch as in claim 6 wherein said electrode patch comprises a metal foil patch and wherein said electrode patch with a liquid crystal layer applied thereon is disposed on and within a larger, adhesively-backed, flexible insulator patch.

8. A conductive electrode patch as in claim 7 wherein said metal foil patch includes an electrical connector affixed thereto with a snap-on connector terminal extending back through an aperture in said flexible insulator patch so as to be accessible when the patch is adhesively affixed to said skin surface.

9. A conductive electrode patch as in claim 6 further comprising a releasable liner covering otherwise exposed adhesive until the liner is removed preparatory to affixation to said skin surface.

10. An apparatus for therapeutic or diagnostic applications in medical or veterinary use which may be adhesively affixed to the external body surface of a subject prior to the application of electrode preparations between the body surface and the electrode, said apparatus comprising:
    a conductive layer having an electrical connection terminal for transferring electrical signals to/from the subject via a first side of the conductive layer and an electrode preparation material;
    a temperature responsive liquid crystal layer affixed to a second opposite side of said conductive layer for measuring the physiological response of the body surface;
    an adhesive layer attached to the conductive layer with said liquid crystal layer also being affixed thereto for holding same in place on the body surface of a subject such that said first side is adjacent the body surface and said liquid crystal layer on the opposite side is visible;
    a releasable liner protectively covering the otherwise exposed adhesive surface of said adhesive layer until the liner is removed to permit affixation to said body surface.

11. An apparatus as in claim 10 wherein:
    said conductive layer comprises a metal foil patch;
    said adhesive layer comprises an adhesive-backed, flexible relatively larger insulator patch;
    said metal foil patch with said liquid crystal layer applied thereon being disposed on and within the adhesively-coated side of said insulator patch.

12. An apparatus as in claim 11 further comprising a snap-on electrical connector terminal affixed to said metal foil and extending back through an aperture in said insulator patch for access through the other side thereof.

* * * * *